United States Patent [19]

Pagani et al.

[11] Patent Number: 4,758,311
[45] Date of Patent: Jul. 19, 1988

[54] METHOD FOR AVOIDING THE CORROSION OF THE STRIPPERS IN THE UREA MANUFACTURING PLANTS

[75] Inventors: Giorgio Pagani, Milan; Giuseppe Faita, Novara; Ubaldo Grassini, Busto Arsizio, all of Italy

[73] Assignee: Montedison S.p.A., Milan, Italy

[21] Appl. No.: 48,458

[22] Filed: May 11, 1987

Related U.S. Application Data

[63] Continuation-in-part of Ser. No. 882,435, Jul. 7, 1986, abandoned, which is a continuation of Ser. No. 752,004, Jul. 5, 1985, abandoned, which is a continuation of Ser. No. 549,504, Nov. 7, 1983, abandoned, which is a continuation-in-part of Ser. No. 468,888, Feb. 23, 1983, abandoned.

[30] Foreign Application Priority Data

Jun. 3, 1982 [IT] Italy ............................. 21666 A/82
Aug. 25, 1982 [IT] Italy ............................. 22962 A/82

[51] Int. Cl.$^4$ ............................................. B01D 3/34
[52] U.S. Cl. ......................................... 203/7; 203/73; 203/86; 203/89; 203/DIG. 9; 159/47.2; 159/49; 564/68; 564/73
[58] Field of Search ............... 203/7, 49, 73, 86, 89, 203/DIG. 9, 71, 72; 159/47.2, 49; 564/68, 73; 202/267 R, 236

[56] References Cited

U.S. PATENT DOCUMENTS

| | | | |
|---|---|---|---|
| 1,986,973 | 1/1935 | Hetherington et al. | 564/68 |
| 2,727,069 | 12/1955 | Van Waes | 564/68 |
| 3,488,293 | 1/1970 | Hong et al. | 564/68 |
| 3,574,738 | 4/1971 | Mavrovic | 564/68 |
| 3,720,548 | 3/1973 | Barake et al. | 148/6.14 R |
| 3,954,861 | 5/1976 | Guadalupi et al. | 564/68 |
| 4,208,347 | 6/1980 | Pagani | 564/70 |
| 4,269,997 | 5/1981 | Pastomerlo | 564/67 |
| 4,301,299 | 11/1981 | Inoue et al. | 564/68 |
| 4,311,856 | 1/1982 | Inoue et al. | 564/68 |
| 4,321,410 | 3/1982 | Ono et al. | 564/67 |

FOREIGN PATENT DOCUMENTS

| | | | |
|---|---|---|---|
| 0765031 | 8/1971 | Belgium | 564/70 |
| 1185944 | 3/1970 | United Kingdom | 564/67 |
| 1341497 | 12/1973 | United Kingdom | 564/67 |
| 0739047 | 6/1980 | U.S.S.R. | 203/7 |

OTHER PUBLICATIONS

General Organic, Belgian Report, Dec. 1963, p. 3.
European Chemical News; Jan. 17, 1969 ("urea supplement"); pp. 17–20.

*Primary Examiner*—S. Leon Bashore
*Assistant Examiner*—Virginia Mandharan
*Attorney, Agent, or Firm*—Stevens, Davis, Miller & Mosher

[57] ABSTRACT

A method for passivating the surface of the strippers of the urea plants, where the temperatures are very high, where the pressures range from 120 to 240 Kg/cm$^2$ and where the effluent process flow from the synthesis reactor undergoes one or more falling-film evaporations, preferably in countercurrent with a driving gas consisting of NH$_3$ or CO$_2$, characterized by the fact that the passivation is carried out by means of a sinergistic combination of oxygen, preferably injected into the bottom of at least one stripper, and of a second passivating agent, preferably injected into the process flow entering the head of at least one stripper, wherein said second passivating agent is injected in the liquid state or as a liquid solution, before or contemporaneously to the start of the evaporation.

4 Claims, 2 Drawing Sheets

METHOD FOR AVOIDING THE CORROSION OF THE STRIPPERS IN THE UREA MANUFACTURING PLANTS

This application is a continuation-in-part of application Ser. No. 882,435, filed July 7, 1986, now abandoned, which is a continuation of 752,004 filed July 5, 1985, now abandoned, which is a continuation of 549,504 filed Nov. 7, 1983, now abandoned, which is a continuation-in-part of 468,888 filed Feb. 23, 1983, now abandoned.

BACKGROUND OF THE INVENTION

The aqueous urea solutions containing non-reacted reactants ($NH_3$ and ammonium carbamate), as well as the solutions of carbamate itself, are strongly corrosive, at the high temperatures, with respect to the metal surfaces lapped by such liquids, and, in spite of all the technological expedients performed until now, heavy corrosion problems must still be faced, particularly in the stripping devices, typical of the modern high temperature and high pressure processes for the manufacture of urea. In general, the most showy corrosion phenomena occur in the uppermost portion of said strippers, where the most part of the heat is supplied and where the evaporation of the non-reacted reactants reaches its highest point, and the traditional addition of oxygen (also in considerable amounts), as a passivation agent, into the bottom of the strippers, does not allow to avoid such phenomena.

The passivation by means of gaseous agents—for instance air—allows to reach a satisfactory level of protection on the surfaces wetted by a non-evaporating liquid and in all parts exposed to condensing vapors; such passivation however does not protect completely the critical points of the modern urea processes, which use strippers consisting of falling-film heat-exchangers. The best known of such processes is the so-called I.D.R. process described in Pagani U.S. Pat. No. 4,208,347.

Belgian Pat. No. 625,397 teaches how to passivate the internal surfaces of a reactor for the synthesis of urea, consisting of a stainless steel containing up to 19% by weight of Cr and 14% by weight of Ni, and describes the use of oxygen, as a passivating agent, at 180° C. and 270 $Kg/cm^2$, while suggesting generically to replace oxygen by other passivating agent, e.g. hydrogen peroxide, alkali metal peroxides and alkaline earth peroxides.

OBJECT OF THE INVENTION

When the modern technology has come through, pivoted on falling-film strippings, countercurrently with $NH_3$ or $CO_2$ streams, at very high temperatures and at pressures from 120 to 240 $Kg/cm^2$, a strongly anomalous behaviour of the metallic surfaces did surprisingly happen: the low corrosion rate inside of the synthesis reactor, where practically all the process fluid is in the liquid state, was more than balanced by an extremely great corrosion in the head of the stipping columns, where the process fluid is present as evaporating liquid, at temperatures which can be higher than the reactor's temperature.

An object of the invention is to avoid the drawbacks hereinabove; other objects will be apparent from the description hereinafter.

DISCLOSURE

In its most general form, the invention concerns a method for passivating the surface of the strippers of the urea manufacturing plants, where the temperatures are very high, where the pressures range from 120 to 240 $Kg/cm^2$, and where the effluent process flow from the synthesis reactor undergoes one or more falling-film evaporations, preferably in countercurrent with a driving gas consisting of $NH_3$ or $CO_2$; the method is characterized by the fact that the passivation is carried out by means of a synergistic combination of oxygen, preferably injected into the bottom of at least one stripper, and of a second passivating agent preferably injected into the process flow entering the head of at least one stripper, wherein said second agent is injected in the liquid state or as a liquid solution, before or contemporaneously to the start of the evaporation, and is selected from the group comprising $H_2O_2$, $NH_4NO_2$, alkali metal or alkaline earth nitrites, alkali metal persulfates, $(NH_4)_2S_2O_8$, $KTcO_4$, alkali metal perborates, peracetic acid and organic peroxides.

The term "oxygen" comprises oxygen as such ($O_2$) or air, optionally enriched by $O_2$, or by any other oxygen-containing gas.

The passivation methods of the present invention have led to excellent results, either on a pilot plant or on an industrial scale, either in the lowermost or in the uppermost portion of the strippers, said portions being frequently stressed by strongly differentiated corrosions.

Furthermore, as a consequence of this novel method, not only are falling-film strippers better protected, but also other parts of the urea-manufacturing plant, as e.g., some of the transfer pipes, exposed to the same operative conditions and particularly to the contact with evaporating process streams, are better protected.

PREFERRED EMBODIMENTS

According to preferred, but non-limiting, embodiments of the invention, the stripping pressure is substantially the same pressure of the synthesis reactor and the stripping is carried out in two subsequent steps, the first step being performed countercurrently to a $NH_3$ stream and the second counter-currently to a $CO_2$ stream. Alternatively the first step may be a self-stripping, namely a merely thermal stripping, without any injection (from the exterior) of a driving gas, the second step being a $CO_2$ stripping; best results are reached when said second agent is hydrogen peroxide, preferably injected in the form of an aqueous solution, especially when injected at least into the process flow entering the head of the second ($CO_2$) stripper.

The whole amount of $H_2O_2$, expressed as active oxygen, should be from 1 to 25 ppm, preferably from 2 to 10 and even better from 4 to 6 ppm, with respect to the effluent process flow leaving the synthesis reactor. Such amount can be subdivided into two portions, the first portion (I) (e.g. 50%) entering the head of the first ($NH_3$) stripper and the second (II) entering the head of the second ($CO_2$) stripper [see FIG. 1, where also a third injection (III) of $H_2O_2$ is provided for, under the point where the recycle (G) reaches the uppermost portion of reactor (R)]; another choice is to inject the whole amount of $H_2O_2$ into the head of the $CO_2$ stripper.

On the contrary, oxygen must be injected at least into the bottom of the second stripper, namely the $CO_2$ stripper, preferably in admixture with the entering $CO_2$ stream, the whole amount of oxygen being from 200 to 2000, preferably from 500 to 2000 ppm, with respect to $CO_2$.

Advantageously, the surfaces lapped by the process flow are consisting of an austenitic stainless steel containing, for instance (by weight), from 16 to 25% Cr, from 13 to 22% Ni and from 2.5 to 3% Mo; better results are however reached when said surfaces are consisting of an austeno-ferritic stainless steel containing, for instance (by weight), from 22 to 25% Cr, from 5 to 7% Ni and from 2.5 to 3% Mo.

Figure 1:
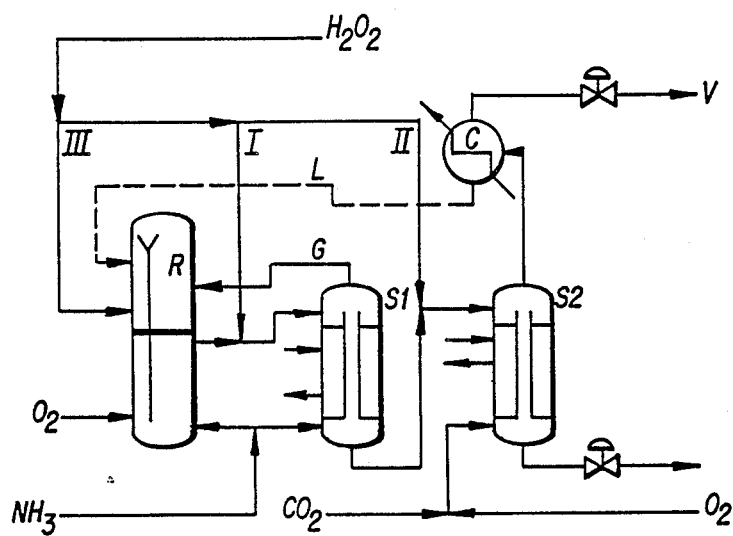
FIG. 1 is a schematic representation of a flow sheet of the process according to the invention.

The drawings on FIG. 1 show a recommendable possibility of carrying out the invention; in said drawings $O_2$ means $O_2$ and/or air, R means reactor (for the synthesis of urea), S1 means first stripper (isobaric with the reactor, in counter-current to $NH_3$, of the falling-film type), S2 means second stripper (isobaric too with the reactor, in countercurrent to $CO_2$, of the falling-film type), C means condenser, V means vent and G and L mean gaseous or liquid recycle.

In the past times the passivating action was believed to be caused in any case by oxygen and only by oxygen, both in the case of injecting air or hydrogen peroxide; $H_2O_2$, however, as well as the other peroxidic compounds dissolved in the process flow, are themselves, per se, passivating agents, more efficaceous than gaseous oxygen, because they cannot be stripped, namely displaced, from the liquid phase.

Should $H_2O_2$ be fed to the bottom of the strippers, it would remain in the liquid flowing out of said bottom and the only chances of passivation would be bound to a very small amount of gaseous oxygen ($O_2$) coming from the partial decomposition of $H_2O_2$. In such a case no protection at all, against the corrosion, would be available in the critical points of the strippers, namely in those points where the process flow is boiling and where, therefore, gaseous oxygen ($O_2$) cannot be absorbed or can be absorbed only with extreme difficulty.

Our invention, on the contrary, allows to exploit completely the passivating activity of $H_2O_2$ and of the other peroxidic substances hereinabove, as well as their poor or null volatility and their sufficiently long persistence (without decomposition) in the boiling liquid wetting the surfaces of the strippers.

At the same time our invention allows a steady protection of the surfaces exposed to the action of gases, because of the injection of gaseous oxygen (or air or enriched air and so on) on the very bottom of the stripper; from a theoretical point of view, also the gaseous oxygen coming from partial decomposition of $H_2O_2$ could engender passivation of the so called gas surfaces, namely of the surfaces exposed only to the corrosive action of gases, but such gaseous oxygen could not replace the action of undecomposed $H_2O_2$ in the so called liquid zones.

There is therefore a big difference between the two possible injections of $H_2O_2$ (into the bottom or into the head of the strippers). In the first case (bottom injection, namely injection into the point where, according to the prior art, oxygen and $CO_2$ have to be fed), the only portion of $H_2O_2$ that could be exploited is the decomposed portion.

In the other case (head injection, corresponding to our invention), the exploited part is the undecomposed portion; the longer it remains in the liquid phase, performing its intrinsic passivating action, the more it shows considerable value from an industrial point of view.

Before reporting the examples hereinafter, it is likely to be suitable to suggest, in some cases, to carry out a pre-treatment of the surfaces, according to the teachings of U.S. Pat. No. 3,720,548.

The following examples illustrate the invention without limiting however in any case its scope.

EXAMPLE 1

The test was carried out on specimen consisting of austenitic stainless steel AISI 316 L UREA GRADE (Werkstoff No. 1.4404/1.4435) containing (by weight):

| C | ≦0.030% | Mn | 1.5 to 2% |
|---|---|---|---|
| S | ≦0.015% | Cr | 16.5 to 17.5% |
| P | ≦0.020% | Ni | 13 to 15% |
| Mo | 2.5 to 3.0% | | | and having 100×100×3 mm dimensions.

The specimen were placed in the liquid zone, in contact with th evaporating gases, within the head of an isobaric falling-film stripper of a IDR urea cycle (countercurrently with $CO_2$), of the type described in example 10 of U.S. Pat. No. 4,208,347 (to the Applicant), where the temperature is about 210° C. and the pressure 200 Kg/$cm^2$ (see FIG. 1).

Besides short runs of a few days, while the passivation was performed merely with 500 ppm of $O_2$ (with respect to $CO_2$), long and continuous runs, also of some months, were carried out by passivating the $CO_2$ stripper with a synergistic combination of the same 500 ppm of $O_2$ hereinabove (added to the $CO_2$ and calculated with respect to $CO_2$) and of 4 ppm of $H_2O_2$ (added to the product to be stripped, expressed as active oxygen and calculated with respect to the total flow rate of the process flow leaving the reactor).

An average corrosion rate of 40 mm/year was noted when the passivation agent was merely $O_2$, but a corrosion rate of only 0.1 mm/year was observed when the $O_2$+$H_2O_2$ combination was used. In the second case the stripper walls showed a quite satisfactory appearance, after a $O_2$+$H_2O_2$ passivation, also after a 1 year run.

Said inner walls of the stripper were consisting of an austenitic stainless steel 25/22/2 (Werkstoff No. 1.4466/1.4465), commercially known as 2 RE 69 (SANDVIK) pipe size), or as 254 SFER (AVESTA) (plate size), and containing (by weight):

| C | ≦0.020% | N | 0.10 to 0.15% |
|---|---|---|---|
| S | ≦0.015% | Cr | 24 to 26% |

-continued

| Mn | 1.5 to 2% | P | ≦0.020% |
| Ni | 21 to 23% | Si | ≦0.4% |
| Mo | 2 to 3% | | |

The amount of Fe in the urea solution obtained, according to the invention, on the bottom of the stripper, was lower than 1 ppm (with respect to urea alone).

EXAMPLE 2

Example 1 was repeated, while raising the $O_2$ amount up to 2000 ppm (with respect to the fed in $CO_2$); quite analogous results were obtained.

EXAMPLES 3 and 4

Examples 1 and 2 were repeated, while raising the amount of $H_2O_2$ up to 6 ppm (expressed as active oxygen and calculated with respect to the total flow rate of the process flow leaving the reactor); quite analogous results were obtained.

EXAMPLES 5 and 6

Example 1 and 2 were repeated, while lowering the amount of $H_2O_2$ down to 2 ppm; quite analogous results were obtained.

EXAMPLE 7

Example 1 was repeated, while using specimen of the following austenoferritic stainless steels:

(A) Werkstoff No. 1.4462, commercially known as SAF 2205 (SAND-VIK), containing (by weight):

| C | ≦0.03% | Mn | ≦2.0% | N | 0.14% |
| Cr | 22% | P | ≦0.03 | Si | ≦0.080% |
| Ni | 5.5% | S | ≦0.02% | Mo | |

(B) Temptative type of steel, commercially known as URANUS-47 (Creusot Loire), containing (by weight):

| C | <0.03% | Mo | 3% | N | 0.17% |
| Cr | 25% | Ni | 7% | | |

Corrosion rates of about 4 mm/year were noted, when the passivating agent was merely $O_2$, and of only 0.05 mm/year when the synergistic combination $O_2+H_2O_2$ was used.

EXAMPLE 8

Figure 2:
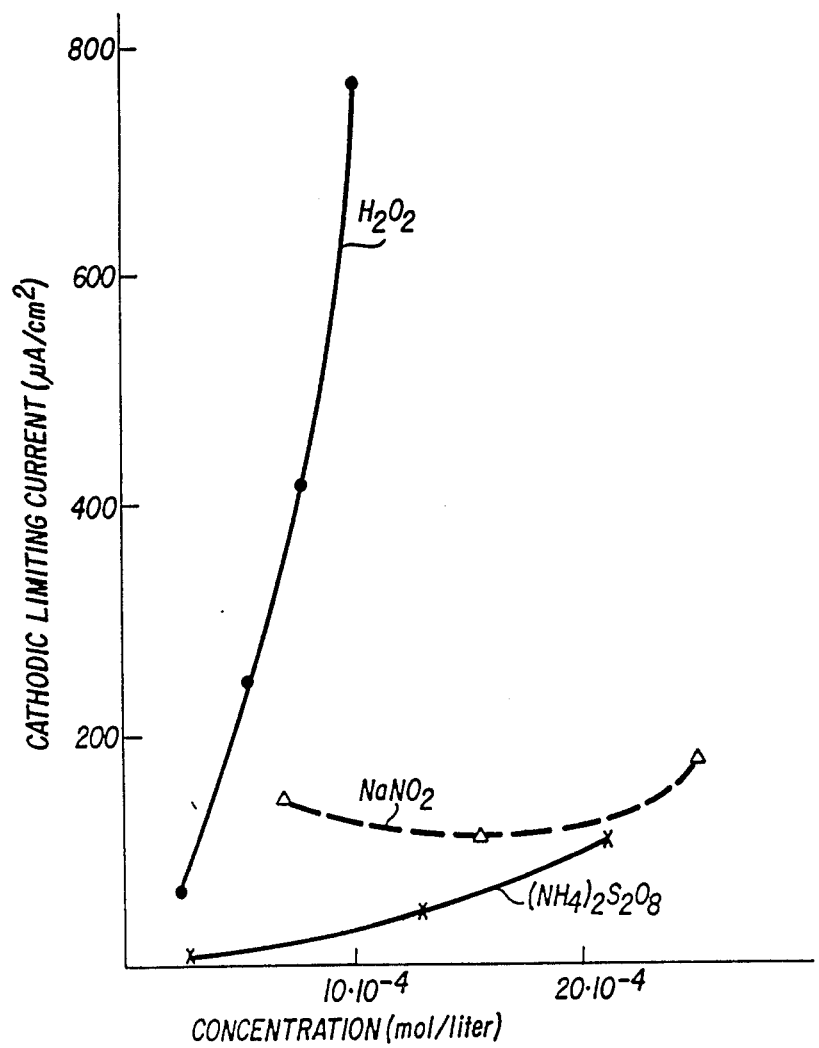
FIG. 2 is a graphic diagram recording a cathodic limiting current (CLR), reported as micro-ampere/$cm^2$, plotted against the concentration of each of the different passivating agents, as tested in example 8 hereinbelow, namely $H_2O_2$, $NaNO_2$ and $(NH_4)_2S_2O_8$.

The present example has allowed to ascertain the activity of different passivating agents. A pressure vessel, supplied with a platinum electrode, was kept at 200° C. and at 200 Kg/cm$^2$ and into the vessel $NH_3$, $CO_2$, $H_2O$ and urea were loaded, the global $NH_3:CO_2$ molar ratio being 5 and the $H_2O:CO_2$ molar ratio being 0.5. The cathodic limiting current (CLR), obtained at constant electrochemical potential of the Pt electrode, was measured under potentiostatic conditions; the values of these currents can be correlated to the passivating activity of the different tested materials. FIG. 2 reports the different CLR versus the concentration of each of the tested passivating agents. Analogous tests, carried out by using pure gaseous $O_2$ (0.2% by weight with respect to the fed in $CO_2$), have allowed to note a CLR between 50 and 60 Microampere/cm$^2$ ($\mu A/cm^2$).

EXAMPLE 9 (comparative)

Example 1 was repeated while adding only $H_2O_2$ and suppressing the injection of $O_2$ on the bottom of the isobaric $CO_2$ stripper.

The corrosion level of the specimen and of all the walls wetted by a liquid phase remained practically unchanged, while some corrosion traces were retrievable on the dry surfaces of the lowermost tube sheet, on the dry lining of the lower head and, finally on the dry lining of the uppermost head of the stripper.

EXAMPLE 10

Figure 3:
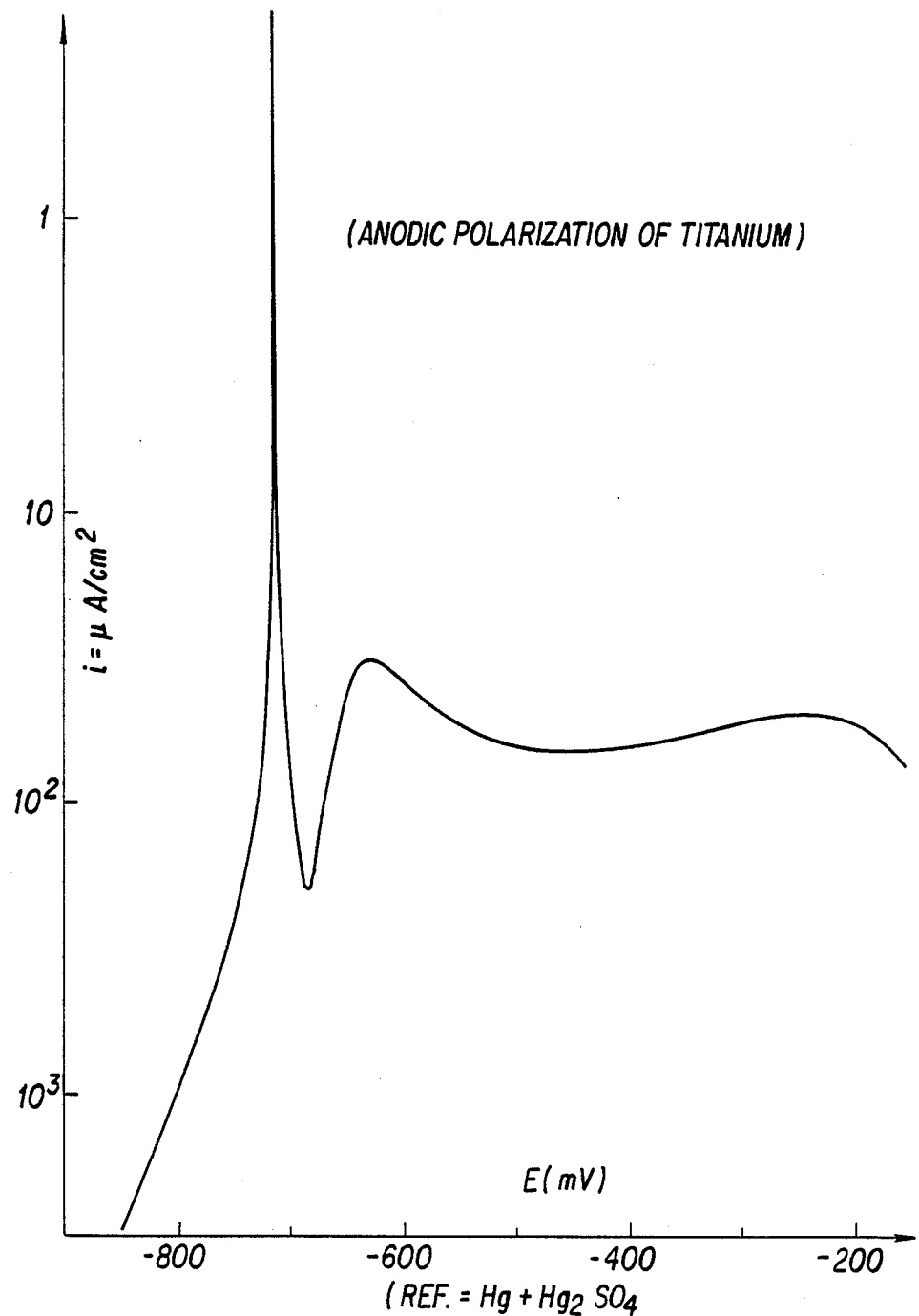
FIG. 3 is a graphic diagram plotting the anodic polarization of titanium, as in example 10 reported hereinbelow, in contact with a fluid which comprises a mixture of $NH_3$, $CO_2$, urea and $H_2O$ (the global $NH_3$:$CO_2$ mole ratio being 4.5 and the $H_2O$:$CO_2$ mole ratio being 0.5) in the absence of $H_2O_2$; the ordinate reports the polarization currents and the abscissa the metal potential with the reference a being mercury sulphate electrode.

A pressure vessel, supplied with a titanium anode, a platinum contro-electrode and a suitable reference electrode, was loaded with $NH_3$, $CO_2$, $H_2O$ and urea (the global $NH_3:CO_2$ mole ratio being 4.5 and the $H_2O:CO_2$ mole rario being 0.5) and was kept many hours at 195° C. and 210 atm. gauge; a curve, showing the anodic polarization of titanium, is reported on FIG. 3. The theoretical (maximum) corrosion rate (any $H_2O_2$ or any other inhibition agent being absent), was approximately 2 mm/year; when an optimum amount of $H_2O_2$ was added, said rate decreased down to 0.28 and even to 0.26 mm/year, but it can be demonstrated that such figure could be lowered down to 0.20 mm/year.

EXAMPLE 11

The former examples were repeated evaluating the corrosion level on the basis of the amount of nickel present in the manufactured urea. The results are recorded on Table A.

TABLE A

| Expedient | Results |
| --- | --- |
| $H_2O_2$ the top (4 ppm) + $O_2$ to the bottom | Practical absence of corrosion on both gas and liquid phase surfaces |
| (500 ppm with respect to $CO_2$) Only $O_2$ to the bottom | Nickel = 0.035 ppm Corrosion absence on the gas phase walls; liquid phase surfaces strongly corroded. |
| (500 ppm with respect to $CO_2$) Only $H_2O_2$ to the top (4 ppm) (4 ppm) | Nickel = 0.450 ppm Corrosion absence on liquid phase walls; traces of corrosion on the gas phase surface Nickel = 0.055 ppm |
| Only $H_2O_2$ to the bottom (4 ppm) | Heavy corrosion on all the walls Nickel = 0.560 ppm |

What we claim is:

1. In a method of passivating the metal surfaces of at least one of two vertical falling-film strippers associated with a synthesis reactor in the manufacture of urea, wherein said strippers work at the same pressure as said synthesis reactor at 120–240 bar and a temperature of 170°–210° C., wherein corrosive, residual reactants containing effluent streams are fed to a head of each of said strippers, wherein said streams substantially contain the whole amount of manufactured urea, and wherein one stripper is fed with a $CO_2$ stream countercurrent to said effluent stream and gaseous oxygen is injected as a passivating agent into a lowermost portion of said one stripper;

the improvement comprising injecting a second passivating agent comprising $H_2O_2$ in aqueous solution into said effluent stream fed to said head of said one stripper.

2. A method according to claim 1, wherein said metal surfaces consist of an austenitic stainless steel containing, by weight, from 16% to 25% Cr, from 13% to 22% Ni, and from 2.5% to 3% Mo.

3. A method according to claim 1, wherein said metal surfaces consist of an austeno-ferritic stainless steel containing, by weight, from 22% to 25% Cr, from 5% to 7% Ni, and from 2.5% to 3% Mo.

4. A method according to claim 1, wherein said metal surfaces comprise titanium or titanium-containing alloy.

* * * * *